United States Patent [19]

Fischell et al.

[11] Patent Number: 4,699,615
[45] Date of Patent: Oct. 13, 1987

[54] FINGER ACTUATED MEDICATION INFUSION SYSTEM

[76] Inventors: David R. Fischell, 62 Stratford Rd., Tinton Falls, N.J. 07724; Tim A. Fischell, 362 Grant Ave., Palo Alto, Calif. 94306

[21] Appl. No.: 796,409

[22] Filed: Nov. 8, 1985

Related U.S. Application Data

[63] Continuation-in-part of Ser. No. 623,058, Jun. 21, 1984.

[30] Foreign Application Priority Data

Jun. 21, 1985 [EP] European Pat. Off. ........ 85107707.3

[51] Int. Cl.⁴ .............................................. A61M 1/00
[52] U.S. Cl. .................................... 604/131; 604/246; 604/141; 604/153; 128/DIG. 12
[58] Field of Search .................... 604/65, 67, 131-133, 604/246, 140, 141, 891, 890, 151, 153, 212; 128/DIG. 12; 417/472, 473

[56] References Cited

U.S. PATENT DOCUMENTS

| | | |
|---|---|---|
| 3,731,681 | 5/1973 | Blackshear et al. ............... 604/141 |
| 3,951,147 | 4/1971 | Tucker et al. ..................... 604/891 |
| 4,146,029 | 3/1979 | Ellinwood, Jr. . |
| 4,193,397 | 3/1980 | Tucker et al. ..................... 604/131 |
| 4,258,711 | 3/1981 | Tucker et al. ..................... 604/131 |
| 4,265,241 | 5/1981 | Portner et al. .................... 604/134 |
| 4,360,019 | 11/1982 | Portner et al. .................... 604/131 |
| 4,373,527 | 2/1983 | Fischell . |
| 4,443,218 | 4/1984 | De Cant, Jr. et al. ..... 128/DIG. 12 |
| 4,482,346 | 11/1984 | Reinicke ..................... 128/DIG. 12 |
| 4,496,343 | 1/1985 | Prosl et al. ......................... 604/141 |
| 4,525,165 | 6/1985 | Fischell ....................... 128/DIG. 12 |

OTHER PUBLICATIONS

"Cancer Pain Relieved by Long-Term Epidural Morphine with Permanent Indwelling System for Self-Admin.," *J. Neurosurg*, Poletti et al, Oct. 1981.

*Primary Examiner*—C. Fred Rosenbaum
*Assistant Examiner*—John D. Ferros
*Attorney, Agent, or Firm*—Fleit, Jacobson, Cohn & Price

[57] ABSTRACT

A Finger Actuated Medication Infusion System (FAMIS) for delivering a dosage of medication into a living body. The FAMIS is fully mechanical and comprises a reservoir, a pump and connecting catheters. The reservoir includes a sealed bellows portion which contains a pressurant and exerts a substantially constant pressure on the medication in the reservoir, regardless of the amount of medication therein. The pump includes a bellows assembly disposed within an equalizing pressure chamber, and will deliver medication through the bellows assembly at a predetermined flow rate independent of ambient temperature, ambient pressure or the amount of medication remaining in the reservoir. The FAMIS design also provides safeguards against inadvertant overdosing, transmission of bacteria into the body and prevents gas bubbles within the reservoir from impeding the flow of medication through an outlet flow restrictor which forms part of the FAMIS pump.

21 Claims, 8 Drawing Figures

FINGER ACTUATED MEDICATION INFUSION SYSTEM

This is a continuation-in-part application of Ser. No. 623,058, filed Jun. 21, 1984.

BACKGROUND OF THE INVENTION

1. Field of the Invention

This invention relates to an improved means for delivering a flow of medication into an animal or a human subject. Although the device described herein is clearly capable of being fully implanted in a living body, it is also readily capable of being used as an extracorporeal means for medication infusion.

2. Description of the Prior Art

In recent years, many advantages have been found in treatments in which medication is infused directly into a patient's body by means of a portable or implantable pumping system. An optimum system for many patients is an implantable medication pumping system that is simple, reliable, small, lightweight, and provides a precise medication infusion rate irrespective of ambient pressure, body temperature or the extent to which the reservoir has been emptied.

One of the earliest implantable pumps is described by P. Blackshear et al. in U.S. Pat. No. 3,731,681. However, the Blackshear et al. device has several disadvantages:

a. It uses the movement of a bellows to dispense the medication. Any bellows will have a spring constant force $F = -kd$, where k is the spring constant of the bellows and d is its displacement from equilibrium. Since drug flow can be directly related to net force of the bellows and this force will vary with the displacement, the medication flow rate will be dependent on bellows displacement.

b. Blackshear's device utilizes a "propellant chamber" which is separated from the medication chamber by a metal plate. The driving force derived from this propellant chamber is independent of ambient atmospheric pressure. The medication flow rate, on the other hand, is related to the difference in pressure between the propellant chamber and ambient pressure. Thus, as ambient pressure changes, the flow rate will change. This is likely to occur due to barometric pressure variations, flying in a jet plane, being at a different altitude, going up in an elevator, diving to the bottom of a swimming pool, etc.

c. The preferred embodiment of the Blackshear et al. device uses a fluorocarbon as the propellant. Fluorocarbons have a strong variatio in vapor pressure as the ambient temperature changes. Thus, if the patient's body temperature increases or decreases, the propellant pressure and thus the medication flow rate will change.

d. The flow rate of the Blackshear et al. pump depends on the resistance of its flow restrictor, which in turn depends on the viscosity of the medication, which is temperature dependent and which varies somewhat with the types and concentration of the medication.

e. To lessen the effects of the bellows spring force, ambient pressure changes and body temperature changes, the Blackshear et al. device, in practice, uses a relatively high pressure propellant. This is cause for concern because a leak of medication is potentially lethal.

f. The high pressure used with the Blackshear et al. device makes refilling the pump reservoir a more difficult task.

g. The Blackshear et al. pump does not allow the patient to alter the flow rate of medication; a feature often desirable for the treatment of medical problems.

In U.S. Pat. No. 4,146,029, Ellinwood describes a number of implanted medication systems. All the devices he describes require power sources and electronic circuitry which make them complex, expensive, and shorten operating life.

R. E. Fischell in U.S. Pat. No. 4,373,527 describes a complex implantable infusion pump which is not only expensive and less reliable, but has a shorter operating life when compared to a simple, fully mechanical pumping system. In addition, the Fischell device also exhibits a variation in flow rate with changing ambient pressure, and to a lesser extent with body temperature and the extent of the fullness of its reservoir.

Recently, the implantable medication pump has shown promise in the treatment of intractable pain, i.e., chronic or remittent pain which is refractory to conventional therapy. Traditionally, a number of different methods have been utilized to treat such pain. These include palliative or "curative" therapy (i.e., surgery, radiation therapy, or chemotherapy), systemically administered narcotics, transcutaneous electrical stimulation, nerve blocks, rhizotomy, radiofrequency induced lesions, epidural or dorsal column electrical stimulation, and central nervous system neurosurgical intervention (e.g. cordotomy, thalamotomy, acupuncture, and hypnosis).

The large number of modes of therapy is generally indicative of the ineffectiveness of these treatments. The three largest groups of patients requiring the treatment of intractable pain are:

Terminal Cancer Patients: Typically with metastases to bone, visceral organs or compression of neural structures; incidence is approximately 200,000 new patients each year.

Chronic Lower Back Pain: Failure after one or more surgical interventions; approximately 200,000 current U.S. cases.

Other Patients: Post-herpetic neuralgia, phantom limb pain, trigeminal neuralgia, etc.

Recently a number of medical centers have been using a new method for the treatment of intractable pain involving the epidural or intrathecal infusion of morphine. As this treatment has gained acceptance, a number of devices have been used. Unfortunately, each has a number of serious disadvantages.

The Broviac catheter, which allows percutaneous infusion, requires the catheter to actually extend through the patient's skin. While this allows injections to be made easily into the cerebro-spinal fluid, the risk of infection and patient discomfort preclude it from being a long term solution for intractable pain.

A large plastic reservoir with associated valves was described by Poletti et al. ("Cancer Pain Relieved by Long-Term Epidural Morphine with Permanent Indwelling Systems for Self Administration," Journal of Neurological Surgery, October 1981). This system utilizes a plastic bag implanted subcutaneously containing a volume of 400 ml of morphine. This approach is potentially dangerous should a leak occur, and requires surgery to replace the bag of morphine as it is not refillable. In addition, the valve system used allows the patient to infuse excessive amounts of morphine with no limit. On the whole, this system is potentially dangerous and not a practicable long-term solution.

SUMMARY OF THE INVENTION

In view of the aforesaid, it is an object of the present invention to provide a fully mechanical Finger Actuated Medication Infusion System (FAMIS) for the infusion of medication into a living body.

Another object of the invention is to provide a FAMIS which provides the patient with a self-controlled flow rate of medication.

A further object is to provide a FAMIS which prevents the patient from overmedicating himself.

Another object is to provide a FAMIS which delivers medication at a flow rate independent of ambient pressure whether it is used externally or within a living body.

Another object is to provide a FAMIS having a positive displacement pump that will deliver into the body the set amount of medication that has been displaced into a bellows pump chamber irrespective of the viscosity of the medication.

Yet a further object is to provide a FAMIS which delivers medication at a flow rate independent of body temperature if implanted, or ambient temperature if used externally.

Another object is to provide a FAMIS which delivers medication at a flow rate independent of the amount of medication remaining in the reservoir.

Still another object of the invention is to provide a FAMIS including a reservoir which may be operated at a pressure slightly below ambient pressure, thus making it easy to fill and less prone to leak than infusion systems operating at positive pressure.

Another object of the invention is to provide a FAMIS that prevents bacteria or pyrogens from passing into the body.

Still another object of the invention is to provide a FAMIS including a flexible interconnection between the FAMIS reservoir and the FAMIS pump which avoids the formation of gas bubbles in the fluid located within the interconnection.

The foregoing and other objects of the invention are achieved by providing a Finger Actuated Medication Infusion System (FAMIS) which is fully mechanical and comprises a reservoir, a pump and connecting catheters. The reservoir includes a sealed bellows portion which contains a pressurant and exerts a substantially constant pressure on the medication in the reservoir, regardless of the amount of medication therein. The pump includes a bellows assembly disposed within an equalizing pressure chamber, and will deliver medication through the bellows assembly at a predetermined flow rate independent of ambient temperature, ambient pressure or the amount of medication remaining in the reservoir. The FAMIS also provides safeguards against inadvertent overdosing, transmission of bacterial infection and the development of gas bubbles within the system.

Other objects and advantages of the invention will become more readily apparent when reference is made to the following description, taken in conjunction with the accompanying drawings.

DETAILED DESCRIPTION OF THE INVENTION

Figure 1:
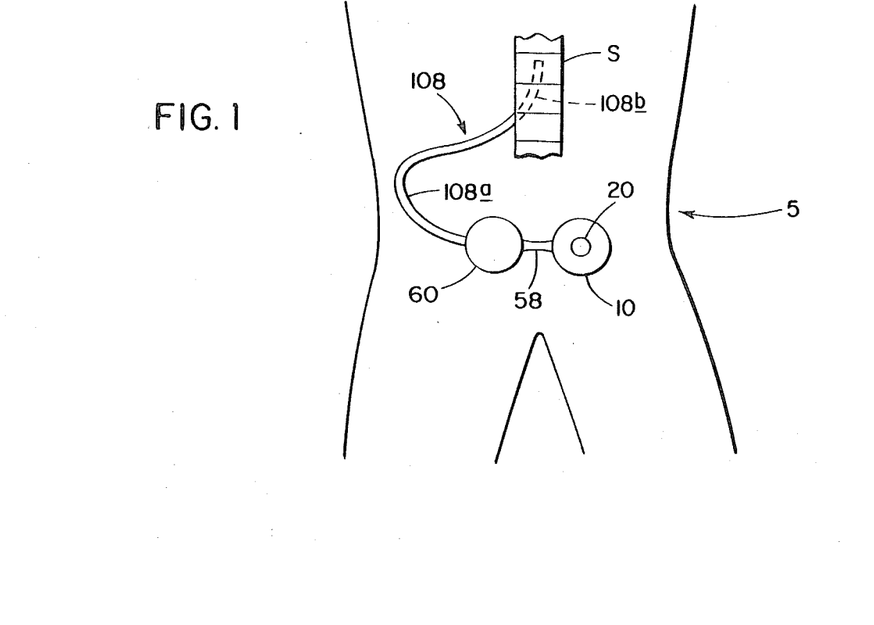
FIG. 1 is a plan schematic view of the present invention implanted in the abdomen of a human patient.

Referring now to FIG. 1, the Finger Actuated Medication Infusion System (FAMIS) is shown generally at 5. In the left side of the patient's abdomen (shown to the right in FIG. 1) just under the skin is located a cylindrically shaped medication reservoir 10 (the FAMIS reservoir) with a central, self-sealing septum 20. An interconnecting catheter 58 connects the reservoir 10 with a pump 60 (the FAMIS pump). The purpose of the FAMIS pump 60 is to pump medication from the reservoir 10 into a catheter 108 and thence into the body. FIG. 1 shows the catheter 108 having a proximal portion 108a attached to the pump 60 and having a distal portion 108b that has entered the spine S. This catheter configuration would typically be used for the infusion of morphine into the spine for the treatment of chronic pain; however, other configurations for treating pain of different origins may also be used.

Figure 2:
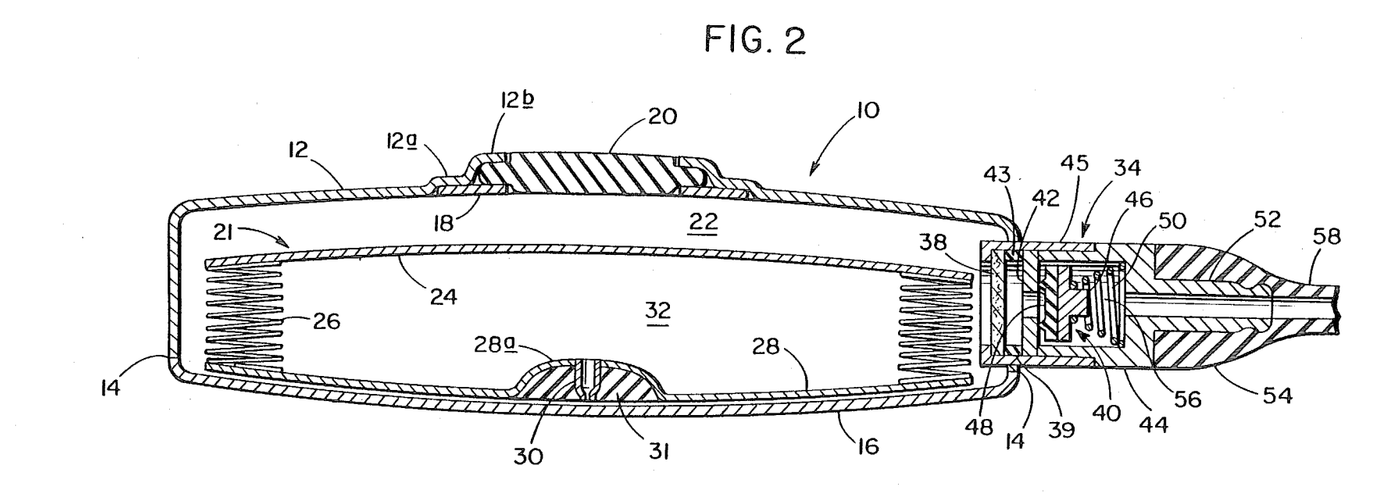
FIG. 2 is a cross-sectional view of a medication reservoir of the present invention.

FIG. 2 illustrates the FAMIS reservoir 10. A to shell 12 is welded together circumferentially at well 14 with the bottom shell 16. The top shell 12 has two protuberances 12a and 12b at its center and a self-sealing septum 20. A septum holding disk 18 is welded into the lower protuberance 12a and compresses the septum 20 against the upper protuberance 12b. The construction of the protuberance 12a, the disk 18 and the septum 20 is such as to form an interior surface that joins smoothly with the top bellows shell 24 of the bellows assembly 21 so as to allow a minimum residual volume of the medication chamber 22 when essentially all the medication is removed from the reservoir 10. The bellows assembly 21 has titanium bellows convolutions 26 that are welded at their bottom to a lower bellows shell 28 and at the top to the upper bellows shell 24. The interior chamber 32 of the bellows assembly 21 contains a pressurant such as FREON 113. When the medication chamber 22 is full, the pressurant in chamber 32 is entirely in the liquid state. When the medication is being pumped into the body, thereby decreasing the volume of the medication chamber 22, the pressurant in chamber 32 increases its volume by converting into a vapor, always at an essentially constant pressure. For example, if FREON 113 is used as the pressurant in chamber 32, the pressure within chamber 32 will be approximately −4 psig at body temperature irrespective of the amount of medication in the medication chamber 32.

If the septum 20 is penetrated by a non-coring hypodermic needle (not shown) which is connected to a vial of medication (not shown) that is vented to atmospheric pressure, then the negative pressure which exists in the bellows chamber 32 and the medication chamber 22 will cause the medication to be sucked out of the vented vial into the medication chamber 22. With a typical titanium bellows construction, the bellows assembly 21 will be at its rest (undeformed) position when it is fully extended, thereby exerting no bellows-caused pressure on the pressurant within chamber 32. When the medication chamber 22 is filled with medication, the bellows convolutions 26 will be fully compressed; therefore, the bellows assembly 21 will exert an additional pressure on the medication fluid due to the spring constant of the bellows convolutions 26. For example, if the convolutions 26 have an outer diameter OD=2.8 inches, an inner diameter ID=2.2 inches, the number of convolutions=10, the convolution thickness=0.002 inches and are made of CP titanium, then at a full compression of 0.4 inches (30 milliliter medication capacity) they will exert an additional pressure of approximately 0.25 psi on the medication fluid. Therefore, the pressure on the medication fluid will remain nearly constant irrespective of the level of medication in the medication chamber 22. However, irrespective of this change in pressure as a function of bellows displacement, the pumping rate depends *only* on the characteristics of the FAMIS pump 60 and not on the displacement pressure variation within the FAMIS reservoir 10.

The septum 20 is preferably made from bromobutyl rubber which, compared to silicone rubber is approximately 100 fold more resistant to the diffusion of gas. Furthermore, the septum is comparatively small in area and extremely thick (approximately 0.150 inch), thereby further reducing the tendency to allow air dissolved in body tissue to diffuse into the negative pressure medication chamber 22. Thus, if the medication is initially deaerated, and the rate of gas diffusion thru the septem 20 is in fact very slow, then no free gas bubbles will be formed in the medication between refills that could interfere with the pumping operation of the FAMIS pump 60.

Returning now to a discussion of the bellows assembly 21, the bottom shell 28 has as its center an indentation 28a which has welded into it a fill pinch tube 30 which is hermetically sealed by welding closed after the chamber 32 has been filled with pressurant. The region below the identation 28a is filled with an elastomer such as silicone rubber to form a plug 31 with a smooth outer surface that decreases the minimum residual volume of the medication chamber 22.

When a pressure that is distinctly lower than the pressure in medication chamber 22 is exerted on the reservoir safety valve 34 (e.g. a pressure of −10 psig) then the valve poppet 40, consisting of a poppet body 46 and poppet elastomer piece 48, will pull away from the valve seat 42 and the medication will be pulled into the connecting tube 58. The fluid will first be drawn through a 0.2 micron filter 38 that serves two purposes: (1) it prevents air bubbles from passing into the connecting tubing 58, and (2) it prevents only bacteria from passing out of the medication chamber 22. Although, in the preferred embodiment, the filter 38 is placed in reservoir 10, it may be placed anywhere upstream of pump 60. The filter 38 is held in place between valve outer cylinder 39 and the valve seat 42 by an elastomer washer 43. A valve spring 50 holds the poppet 40 against the seat 42 so as to require a pressure differential across the poppet 40 of approximately 1.0 psi difference in order to cause flow from the chamber 22 into the valve chamber 56 and then into the connecting tubing 58. The valve 34 has a cylindrical shell 45 and also includes a tubing connector piece 44 which has a cylindrical section 52 that joins to a thickened stress relief section 54 of the interconnecting tubing 58. With the possible exception of the septum 20, all FAMIS elastomer parts are medical grade silicone rubber and all metallic parts are preferably fabricated from CP titanium or a body-compatible titanium alloy such as titanium 6-4.

Figure 3:
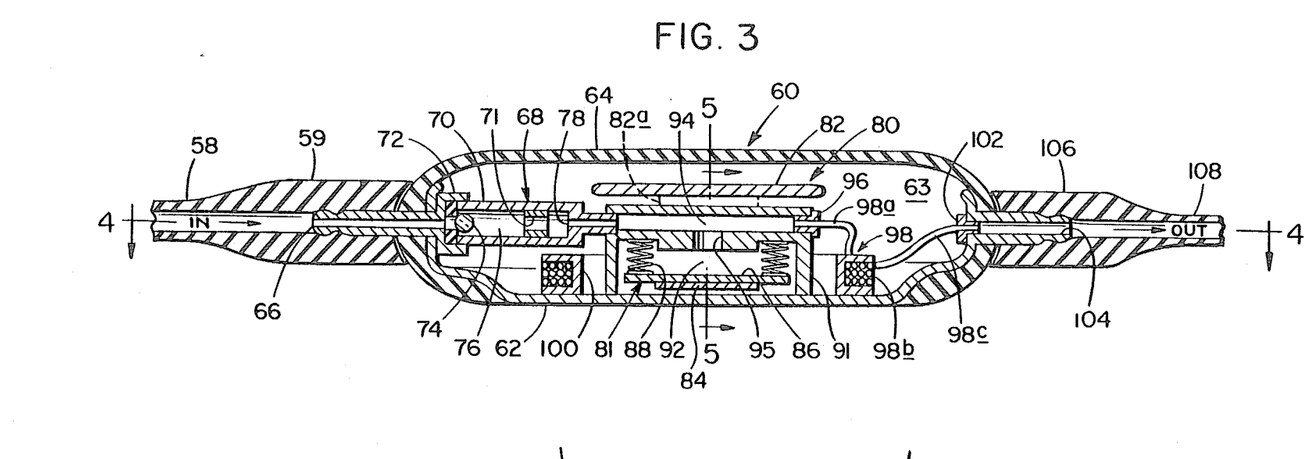
FIG. 3 is a cross-sectional view of a FAMIS pump of the present invention taken along line 3—3 of FIG. 4.
Figure 4:
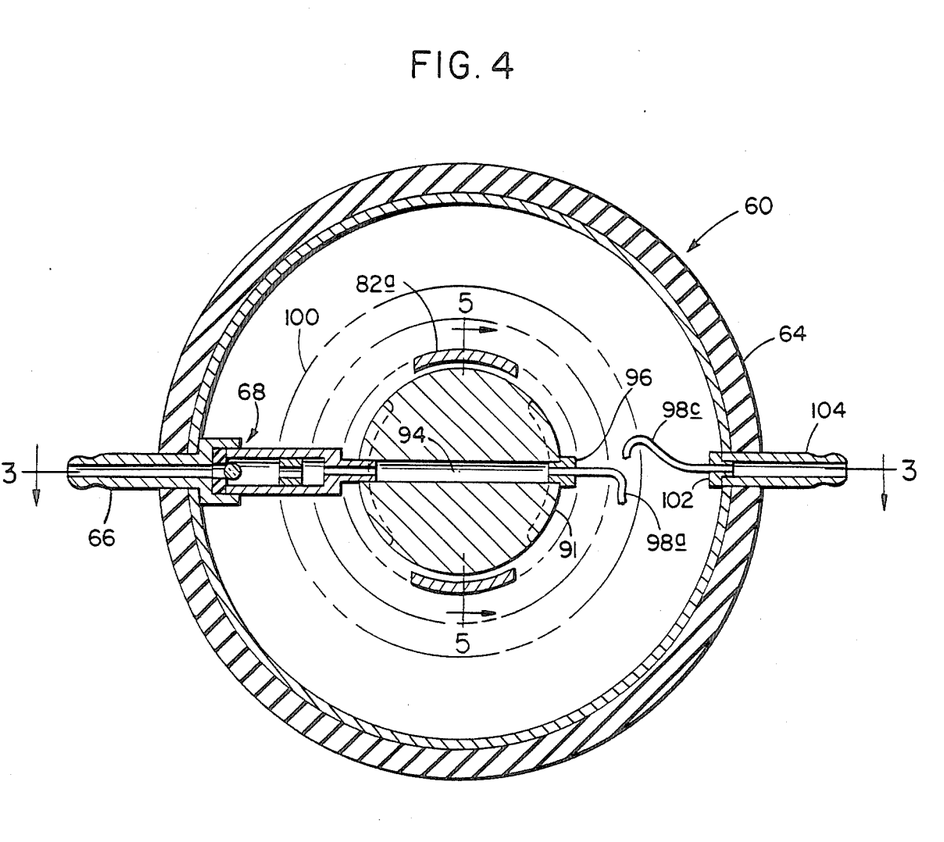
FIG. 4 is a cross-sectional view taken along line 4—4 of FIG. 3.

Referring to FIGS. 3 and 4, pump 60 and its operational characteristics will now be discussed. The medication enters through the connecting tubing 58 which has a thickness stress relief section 59 that joins with the inlet tube 66. The inlet tube 66 is welded into the pump's bottom shell 62 and also joins to the pump inlet check valve 68. The valve 68 consists of a spherical poppet 74 (typically made of sapphire) which closes against a soft elastomer seat 72. The check valve body 70 encloses a valve chamber 76. Four small projections 71 on the interior surface of valve body 70 (two of which are shown in FIG. 3) prevent the poppet 74 from closing off the exit port 78 of the valve body 70 when medication is pulled through the check valve 68. These projections 71 each occupy less than 30° of the circumference of the interior surface of the valve body 70, and therefore will not obstruct the flow thru chamber 76.

When the medication passes through the check valve 68 it enters the pump manifold chamber 94 of the bellows pump 80 having the bellows 81. The bellows pump 80 operates in the following way: (1) the patient in whom the Famis 5 is implanted presses with one or more fingers through the skin just over the site of the implanted pump 60; (2) the elastomer diaphragm 64 is then pushed at its center onto the top of bottom actuator 82; (3) force is then exerted on bellows bottom attachment 84 through the actuator extenders 82a; (4) the bottom movable plate 86 of the bellows convolutions 88 is then forced downward because the plate 86 is rigidly joined to the attachment 84; (5) the bellows convolutions 88 then expand increasing the volume of the pump chamber 92 and pulling medication through the inlet check valve 68, out the valve exit port 78, into the pump manifold 94, through the pump chamber inlet port 95 and finally into pump chamber 92. As is shown in FIG. 3, the entire bellows pump 80 structure is rigidly attached to the bottom shell 62 by the pump body 91.

The convolutions 88 are in their rest (i.e., undeformed) position when fully contracted. Thus, when the bellows actuator 82 is pushed down, fully extending the convolutions 88, and then released, a positive pressure is created in the bellows pump chamber 92 that forces the medication out of the pump manifold 94 through a fluid flow restrictor tube 98 and finally into the body. Specifically, an end fitting 96 containing the inlet section 98a of the restrictor tube 98 is joined with the exit port of the pump manifold 94. The center section 98b, which includes most of the length of the flow restrictor 98, is contained within a cylindrically shaped restrictor tube coil form 100 having a "U"-shaped cross section. Finally, the medication passes through the exit section 98c of the restrictor 98 which terminates in end fitting 102. End fitting 102 joins with pump exit tube 104 which in turn joins with thickened stress relief section 106 of the outlet catheter 108 from whose distal tip the medication finally enters the body. By virtue of this design, the instantaneous flow rate of medication from pump 60 is determined by the spring rate of the convolutions 88, and the resistance of the flow restrictor 98.

Between the pump diaphragm 64 and its bottom shell 62 is the equalizing pressure chamber 63 which contains a fluid such as sterilized normal saline solution. Because this solution is incompressible, it will cause any variation of ambient pressure exerted on the diaphragm 64 also to be exerted on the bellows pump 80. Thus, the rate of flow out of the FAMIS pump 60 will be independent of the ambient pressure in which the body is immersed. Furthermore, since the characteristics of the titanium convolutions 88 and the flow restrictor 98 are essentially independent of temperature over the range of possible body temperatures, the FAMIS pump flow rate is also independent of ambient temperature.

Because of the construction of the outlet valve 34 of the reservoir 10 and the inlet valve 68 of the pump 60, the fluid within the interconnecting tube 58 between the reservoir 10 and pump 60 will always be at a pressure equal to or greater than zero psig except during that instant when the bellows pump is activated. Typically, since there is no spring to cause the poppet 74 to seal against the seat 72, the pressure in the fluid within the catheter 58 will approach the value of the positive pressure within the bellows pump chamber 92. Thus, even though the interconnecting tube 58 is preferably made of thin-walled, flexible silicone rubber, it is unlikely that gas will diffuse thru the wall into the fluid within the interconnecting tube 58, and thereby create free gas bubbles that could clog the flow restrictor 98.

Figure 5A:
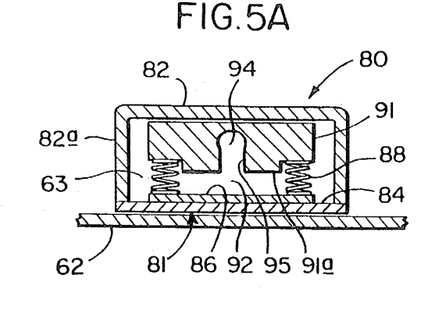
FIG. 5A is a cross-sectional view taken along line 5—5 of FIGS. 3 and 4 showing the FAMIS pump in its fully expanded position.
Figure 5B:
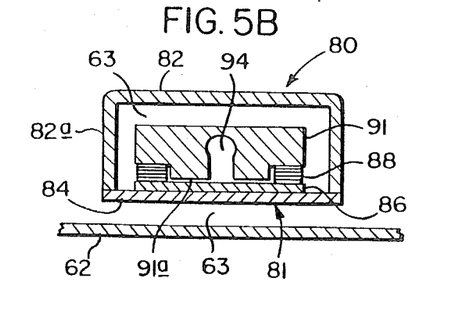
FIG. 5B is a cross-sectional view taken along line 5—5 of FIGS. 3 and 4 showing the FAMIS pump in its fully contracted position.

FIGS. 5A and 5B illustrate the bellows pump 80 in greater detail. FIG. 5A shows the bellows pump 80 in its fully extended position (i.e., maximum volume of the bellows chamber 92). FIG. 5B shows the fully retracted position of the bellows pump 80 (i.e., the minimum volume of the bellows chamber 92). From FIG. 5A we see that when the bellows volume is a maximum, the attachment 84 is in contact with the bottom shell 62 of the FAMIS pump 60. In FIG. 5B we see that the extended surface 91a of the pump body 91 causes the residual volume of the bellows pump chamber 92 to be extremely small when the bellows pump 80 is emptied (i.e., in its fully retracted position). The equalizing pressure chamber 63 includes the space around the bellows convolutions 88 and the attachment 84. Hence, ambient pressure is impressed upon the bellows assembly 80 through the fluid in chamber 63.

Figure 6:
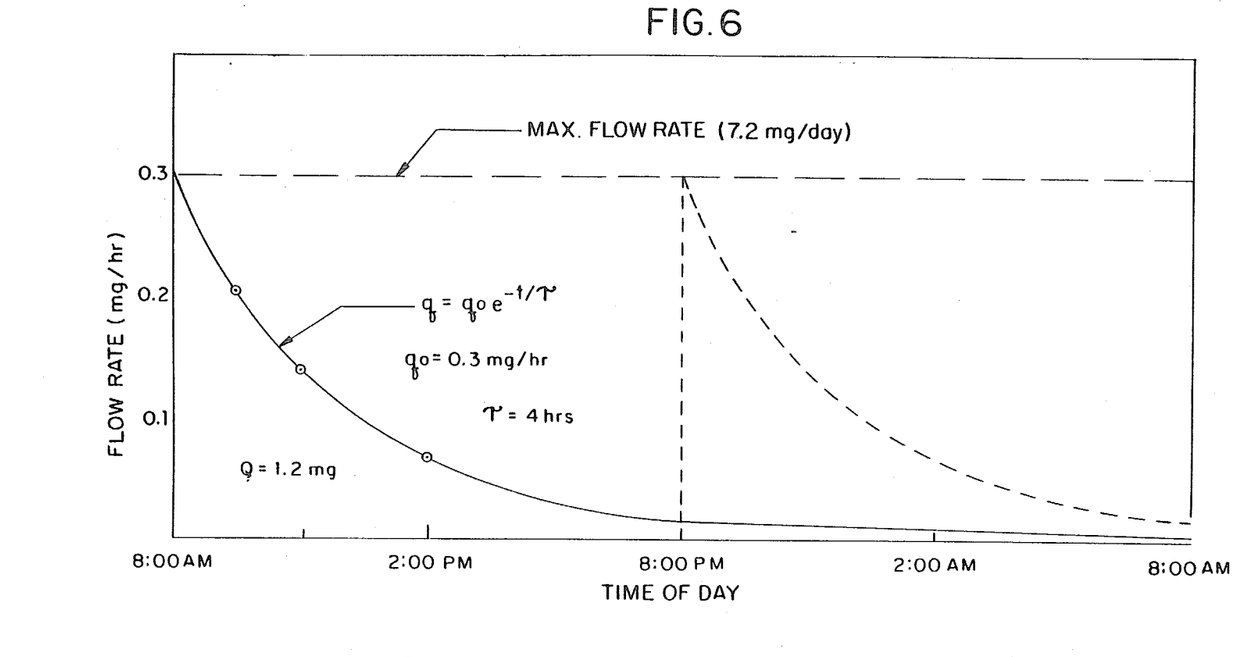
FIG. 6 graphically illustrates a typically medication flow rate pattern of the present invention as a function of time of day.

FIG. 6 shows the flow rate of medication from the FAMIS pump 60 as a function of time of day. Specifically, FIG. 6 shows typical flow patterns for the infusion of morphine into the CSF of the spine (i.e., the intrathecal infusion of morphine). This infusion therapy typically is used for the treatment of terminal cancer pain. Normally 1 mg per milliliter morphine solution is used with an infusion rate of 1 to 5 mg per day of morphine required to minimize pain. Therefore, a fluid volume of 1 to 5 milliliters of morphine solution is used each day.

The flow rate of a fluid from the bellows pump 80 through a flow restrictor 98 is given by:

$$q = q_0 e^{-t/\tau}$$

where
$q$ = flow rate (mg/hr)
$q_0$ = flow rate at full bellows extension (mg/hr)
$e$ = 2.718
$t$ = time (hr)
$\tau$ = time constant (hr)

The spring rate of the bellows 81, its maximum extension, and the resistance of the flow restrictor 98 can be set to provide a variety of values of the maximum flow rate $q_0$. Higher spring rates and greater extensions of the bellows 81 will result in higher values of $q_0$. The higher the flow resistance, the lower will be the value of $q_0$. For a typical bellows spring rate, maximum extension and flow restrictor, one could set the value of $q_0$ to be 0.3 mg/hr which is 7.2 mg/day.

The time constant is also a function of the bellows spring rate and restrictor flow resistance, but is independent of the maximum bellows deflection. Thus, independent setting of $\tau = 4$ hrs. could be accomplished while setting the value of $q_0 = 0.3$ mg/hr.

Returning now to FIG. 6, we see that if the FAMIS pump 60 is actuated through the skin at 8:00 a.m., it will provide an initial morphine flow rate of $q_0 = 0.3$ mg/hr. The flow rate will then fall off exponentially (as shown by the solid line curve in FIG. 6) with its value reaching $q_0/e$ in one time constant of four hours. Therefore, at noon (12:00−8:00=4 hrs.) the flow rate will be $q_0/e = 0.3/2.718 = 0.110$ mg/hr. The total amount of morphine, Q, that can be pumped into the body by a single stroke of the bellows pump 80 (FIG. 3) is:

$$Q = \int_0^\infty q\,dt = q_0 \int_0^\infty e^{-t/\tau}dt$$

or $$Q = q_0 \tau$$

Therefore, where $q_0 = 0.3$ mg/hr and $\tau = 4$ hrs., $Q = 1.2$ mg. That is, each pump stroke will deliver at most 1.2 mg of morphine into the CSF.

If another pump stroke is delivered at 8:00 p.m., as shown by the dotted line curve in FIG. 6, the total flow rate in a 24 hour period from 8:00 a.m. on one day to 8:00 a.m. on the next day will be given by:

$$Q_{24\,hrs} = \int_0^{12} q\,dt + \int_0^{12} q\,dt = 2\int_0^{12} q\,dt$$

or, $$Q_{24\,hrs} = -2q_0\tau[e^{-T/\tau}]\int_0^{12} = 2.28\,mg$$

Therefore, two pushes of diaphragm 64 do not provide $2 \times 1.2$ mg = 2.4 mg, but in fact provide only 2.28 mg. This occurs because the tail end of the delivery of the 8:00 a.m. push is lost when the pump is finger actuated for a second time at 8:00 p.m. In fact, if the pump is pushed by the patient 1,000 times a day, the maximum flow into the body cannot exceed the maximum flow rate $q_0 = 0.3$ mg/hr $\times$ 24 hrs = 7.2 mg/day. Therefore, the patient cannot overdose himself with morphine or any other medication that has been put into the FAMIS reservoir 10 as long as $q_0$ is set at a safe level.

Figure 7:
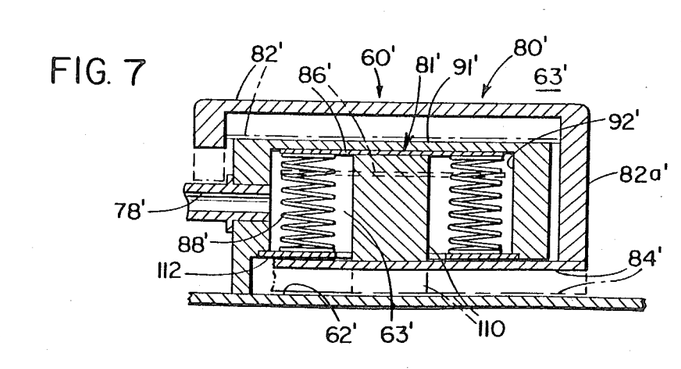
FIG. 7 illustrates an alternative form of a bellows pump of the present invention.

FIG. 7 shows an alternative form of a bellows pump 80' which utilizes a bellows 81' that operates by being placed in compression and which then expands in a medication infusion operation, as compared to being expanded and then retracting to a compressed state, as was described for the bellows 81 shown in FIGS. 3, 5A and 5B. FIG. 7 shows the bellows 81' in its expanded rest position in solid lines, i.e., not compressed. Medication fluid enters the pump chamber 92' from the exit port 78' of an inlet valve (not shown) when the pressure through the skin and then through an elastomer septum (not shown), as illustrated by the embodiment of the invention in FIG. 3.

Downward movement of the bellows actuator 82' causes the actuator extenders 82a' (only one shown) to be forced downward, causing the bottom attachment 84', the cylinder 110 and the bellows upper movable plate 86', which are all interconnected, to be forced downward into positions as illustrated by broken lines in FIG. 7. This causes the bellow convolutions 88', the interior of which is in communication with the equalizing chamber 63' as illustrated at 112, to be compressed, thus increasing the volume of the pump chamber 92'. When the force of the bellows actuator 82' is removed, the bellows convolutions 88' will tend to expand (i.e., move upward). This exerts a pressure within the pump chamber 92' tending to force the medication fluid back out through the valve port 78', which also is connected to an inlet side of a flow restrictor (not shown). The pump body 91' is fixedly attached to a bottom shell 62' of the FAMIS pump 60' at typically two places around the periphery of the pump body.

An important advantage of the compression-expansion bellows pump 80', which is placed in compression and then expands in a medication infusion operation, can provide a greater displaced volume per convolution as compared with the expansion-retraction bellows 81 of FIGS. 3, 5A and 5B. As a result, the bellows 81' can be constructed with fewer convolutions, providing a more reliable and less costly bellows construction.

Although particular embodiments of the present invention have been illustrated and described, it will be apparent to those skilled in the art that various changes and modifications can be made without departing from the spirit and scope of the present invention. It therefore is the intent to encompass within the appended claims all such changes and modifications that fall within the scope of the present invention.

What is claimed is:

1. An apparatus for delivering a flow of medication over an extended period of time into a living body, said apparatus comprising:
   a medication reservoir for holding said medication in readiness for delivery into said living body;
   pump means for receiving medication from said reservoir and for mechanically delivering said medication at a predetermined decaying dosage rate having a predetermined maximum into said living body over the extended period of time;
   connecting means for facilitating passage of said medication from said reservoir to said pump means and communicating therebetween;
   dosing means disposed within and forming part of said pump means, for providing a predetermined dosage of medication for delivery into the living body, said pump means being manually actuatable with a predetermined stroke to fill said dosing means with said predetermined dosage by drawing medication from said reservoir, and said dosing means being operable to deliver medication into the living body upon release of said pump means; and
   limiting means disposed downstream from said dosing means for limiting the dosage rate and cooperable with said dosing means to limit the dosage to said predetermined maximum, regardless of the number of times said pump means is actuated, thereby ensuring that the maximum dosage of medication is maintained at a safe level for any given period of time.

2. An apparatus for delivering a flow of medication over an extended period of time into a living body, said apparatus comprising:
   a medication reservoir for holding said medication in readiness for delivery into said living body;
   pump means for receiving medication from said reservoir and for mechanically delivering said medication into said living body over the extended period of time;
   connecting means for facilitating passage of said medication from said reservoir to said pump means and communicating therebetween; and
   dosing means disposed within and forming a part of said pump means, for providing a predetermined dosage of medication for delivery into the living body, said pump means being manually actuatable with a predetermined stroke to fill said dosing means by drawing medication from said reservoir, and said dosing means being operable to deliver medication into the living body upon release of said pump means.

3. The apparatus of claim 2, wherein:
   said pump means comprises a top diaphragm and a bottom shell defining an equalizing pressure chamber therebetween;
   said dosing means comprises a bellows assembly;
   said pump means includes an inlet portion and an exit portion, said bellows assembly being disposed adjacent said inlet portion and said exit portion and communicating therewith, said bellows assembly including manually operated actuator means for causing the flow of said medication into said bellows assembly from said reservoir; and
   said inlet portion, said exit portion and said bellows assembly being disposed within said pressure chamber.

4. The apparatus of claim 2, wherein said medication reservoir comprises:
   a top and bottom portion defining a medication chamber therebetween;
   a septum disposed on said top portion for facilitating introduction of said medication into said medication chamber;
   an enclosed bellows assembly disposed within said medication chamber and attached to said bottom portion, said bellows assembly having an interior chamber;
   said interior chamber containing a pressurant, said bellows assembly thereby exerting a substantially constant pressure on said medication regardless of the amount of medication in said medication chamber; and
   a valve assembly communicating with said medication chamber for facilitating removal of said medication from said medication chamber.

5. The apparatus of claim 2, further comprising:
   limiting means disposed downstream from said dosing means for limiting the dosage rate so that the predetermined dosage is delivered to the living body over the extended period of time.

6. The apparatus of claim 2, wherein said pump means includes an incompressible fluid surrounding said dosing means, said predetermined dosage rate thereby being essentially independent of ambient pressure.

7. The apparatus of claim 2, wherein said pump means mechanically delivers said medication into the living body at a predetermined decaying dosage rate.

8. An apparatus for delivering a flow of medication over an extended period of time into a living body, said apparatus comprising:
   a medication reservoir for holding said medication in readiness for delivery into said living body;
   pump means for receiving medication from said reservoir and for mechanically delivering said medication at a predetermined decaying dosage rate into said living body over the extended period of time;
   connecting means for facilitating passage of said medication from said reservoir to said pump means and communicating therebetween;
   dosing means disposed within said pump means for providing a predetermined dosage of medication for delivery into the living body, said pump means being manually actuatable with a predetermined stroke to fill said dosing means by drawing medication from said reservoir, and said dosing means being operable to deliver medication into the living body upon release of said pump means
   said reservoir having a valve assembly connecting with said connecting means, said valve assembly providing a seal for said reservoir and remaining closed except when said pump means is actuated; and
   said pump means including an incompressible fluid surrounding said dosing means, said predetermined dosage rate thereby being essentially independent of ambient pressure.

9. An apparatus for delivering a flow of medication over an extended period of time into a living body, said apparatus comprising:
   a medication reservoir for holding said medication in readiness for delivery into said living body;
   pump means for receiving medication from said reservoir and for mechanically delivering said medication at a predetermined decaying dosage rate into said living body over the extended period of time, said pump means being manually actuatable with a predetermined stroke to fill said pump means by drawing medication from said reservoir, and being operable to deliver medication into the living body upon being released;
   connecting means for facilitating passage of said medication from said reservoir to said pump means and communicating therebetween;
   said reservoir having a valve assembly connecting with said connecting means, said valve assembly providing a seal for said reservoir; and
   said pump means having a valve assembly connecting with said connecting means, said reservoir valve assembly and said pump means valve assembly remaining closed except when said pump means is actuated, said connecting means thereby maintaining a positive pressure therein.

10. An apparatus for delivering a flow of medication over an extended period of time into a living body, said apparatus comprising:
    a medication reservoir for holding said medication in readiness for delivery into said living body;
    pump means for receiving medication from said reservoir and for mechanically delivering said medication at a predetermined decaying dosage rate into said living body over the extended period of time, said pump means being manually actuatable with a predetermined stroke to fill said pump means by drawing medication from said reservior, and being operable to deliver medication into the living body upon being released;
    connecting means for facilitating passage of said medication from said reservoir to said pump means and communicating therebetween; and
    filter means disposed upstream from said pump means for preventing the passage of bacteria and gas bubbles from said reservoir into said pump means.

11. A pump, for use in combination with a medication reservoir, for receiving medication from said reservoir and for mechanically delivering said medication at a predetermined decaying dosage rate having a predetermined maximum into a living body over an extended period of time, said pump comprising:
    dosing means for providing a predetermined dosage of medication for delivery into the living body, said predetermined dosage corresponding to a single, manual actuation of said pump of a predetermined stroke; and
    limiting means disposed downstream from said dosing means for limiting the dosage rate and cooperable with said dosing means to limit the dosage to said predetermined maximum, regardless of the number of times said pump is actuated, thereby ensuring that the maximum dosage of medication is maintained at a safe level for any given period of time.

12. The pump of claim 11, wherein said dosing means comprises a bellows assembly.

13. The pump of claim 12, wherein said dosing means includes a manual actuator means and said bellows assembly has convolutions which are compressed in a rest state, expand in response to manual operation of said actuator means, and retract upon release of said actuator means to cause delivery of said medication into the living body.

14. The pump of claim 12, wherein said dosing means includes a manual actuator means and said bellows assembly has convolutions which are expanded in a rest state, retract in response to manual operation of said actuator means, and expand upon release of said actuator means to cause delivery of said medication into the living body.

15. A manually actuatable pump, for use in combination with a medication reservoir, for receiving medication from said reservoir and for mechanically delivering said medication over an extended period of time into a living body, said pump comprising:
    dosing means for providing a predetermined dosage of medication into the living body; and
    manual actuator means for filling said dosing means with said predetermined dosage of medication with a single predetermined stroke of said actuator means, with said dosing means being operable to deliver the medication into the living body upon release of said actuator means.

16. The pump of claim 15, wherein said pump further comprises:
    a pressure chamber;
    a bellows assembly having convolutions fixedly mounted at one end and connected at an opposite end to a movable support member;
    an actuator plate disposed above said pressure chamber; and means for connecting said actuator plate to said movable support member;

said convolutions of said bellows assembly being operated from a rest state to an operative state by depression of said actuator plate, connecting means and movable support member, to draw medication fluid into said pressure chamber and said convolutions subsequently returning to said rest state upon release of said actuator plate to dispense the medication fluid from said pressure chamber.

17. The pump of claim 15, wherein said pump further comprises:

a top diaphragm and a bottom shell defining an equalizing pressure chamber therebetween;

said dosing means being disposed in said equalizing pressure chamber; and said equalizing pressure chamber including an incompressible fluid, said fluid causing any variation in ambient pressure exerted on said top diaphragm also to be exerted on said dosing means, said medication flow rate thereby being essentially independent of ambient pressure.

18. The pump of claim 15, wherein said pump further comprises:

limiting means disposed downstream from said dosing means for limiting the dosage rate so that the predetermined dosage is delivered into the living body over the extended period of time.

19. The pump of claim 15, wherein said dosing means is a bellows assembly having convolutions which are compressed in a rest state, expand in response to manual operation of said actuator means, and retract upon release of said actuator means to cause delivery of said medication into the living body.

20. The pump of claim 15, wherein said dosing means is a bellows assembly having convolutions which are expanded in a rest state, retract in response to manual operation of said actuator means, and expand upon release of said actuator means to cause delivery of said medication into the living body.

21. The pump of claim 15, wherein said pump mechanically delivers said medication into the living body at a predetermined decaying dosage rate.

* * * * *